(12) United States Patent
Houff

(10) Patent No.: US 10,010,360 B2
(45) Date of Patent: Jul. 3, 2018

(54) STERNUM FIXATION DEVICE AND METHOD

(71) Applicant: Louis Houff, Piperton, TN (US)

(72) Inventor: Louis Houff, Piperton, TN (US)

( * ) Notice: Subject to any disclaimer, the term of this patent is extended or adjusted under 35 U.S.C. 154(b) by 0 days.

(21) Appl. No.: 15/444,469

(22) Filed: Feb. 28, 2017

(65) Prior Publication Data

US 2017/0164991 A1    Jun. 15, 2017

Related U.S. Application Data

(62) Division of application No. 14/153,019, filed on Jan. 11, 2014, now Pat. No. 9,597,132.

(60) Provisional application No. 61/751,821, filed on Jan. 12, 2013.

(51) Int. Cl.
*A61B 17/82* (2006.01)
*A61B 17/84* (2006.01)
*A61B 17/80* (2006.01)

(52) U.S. Cl.
CPC ........ *A61B 17/823* (2013.01); *A61B 17/8076* (2013.01); *A61B 17/842* (2013.01)

(58) Field of Classification Search
CPC ....... A61B 17/82; A61B 17/823; A61B 17/80; A61B 17/84; A61B 17/842
See application file for complete search history.

(56) References Cited

U.S. PATENT DOCUMENTS

| | | | |
|---|---|---|---|
| 1,950,799 A * | 3/1934 | Jones | A61B 17/82 606/286 |
| 4,119,091 A | 10/1978 | Partridge | |
| 4,730,615 A | 3/1988 | Sutherland et al. | |
| 4,896,668 A | 1/1990 | Popoff et al. | |
| 5,139,498 A | 8/1992 | Astudillo Ley | |
| 5,190,545 A | 3/1993 | Corsi et al. | |
| 5,330,489 A * | 7/1994 | Green | A61B 17/82 24/170 |
| 5,702,399 A | 12/1997 | Kilpela et al. | |
| 5,722,976 A * | 3/1998 | Brown | A61B 17/8076 606/281 |
| 5,941,881 A * | 8/1999 | Barnes | A61B 17/8004 606/207 |
| 6,387,099 B1 | 5/2002 | Lange et al. | |
| 7,033,377 B2 * | 4/2006 | Miller, III | A61B 17/823 606/213 |
| 7,537,596 B2 | 5/2009 | Jensen | |

(Continued)

FOREIGN PATENT DOCUMENTS

| | | |
|---|---|---|
| JP | 2003515571 A1 | 5/2003 |
| WO | 2012114360 A1 | 8/2012 |
| WO | 2013003719 A1 | 1/2013 |

OTHER PUBLICATIONS

European Patent Office; Communication pursuant to Article 94(3) EPC; Examination Report; dated Oct. 25, 2016; pp. 1-5; European Patent Office; Germany.

(Continued)

*Primary Examiner* — Christopher Beccia
(74) *Attorney, Agent, or Firm* — Wyatt, Tarrant & Combs, LLP; Stephen C. Hall; Max E. Bridges

(57) ABSTRACT

An apparatus and technique for infernally securing a plurality of bone segments together. The device incorporates a plate-like structure stabilizing the fracture and integrated fasteners to attach straps circumscribing the bone segments.

9 Claims, 11 Drawing Sheets

(56) References Cited

U.S. PATENT DOCUMENTS

| | | |
|---|---|---|
| 2007/0038218 A1 | 2/2007 | Grevious |
| 2007/0123883 A1 | 5/2007 | Ellis et al. |
| 2008/0208205 A1 | 8/2008 | Kraemer |
| 2009/0105717 A1 | 4/2009 | Bluechel |
| 2009/0287215 A1 | 11/2009 | Fisher et al. |
| 2010/0094294 A1 | 4/2010 | Gillard et al. |
| 2010/0211075 A1 | 8/2010 | Stone |
| 2011/0035008 A1 | 2/2011 | Williams |
| 2011/0087295 A1 | 4/2011 | Kubiak et al. |
| 2011/0295257 A1* | 12/2011 | McClellan ............ A61B 17/823 606/74 |
| 2012/0041441 A1 | 2/2012 | Bernstein et al. |
| 2012/0059424 A1* | 3/2012 | Epperly ............. A61B 17/8061 606/281 |
| 2012/0089193 A1* | 4/2012 | Stone ................. A61B 17/0401 606/301 |
| 2012/0221060 A1 | 8/2012 | Blain |
| 2013/0165933 A1 | 6/2013 | Gephart |
| 2013/0172944 A1 | 7/2013 | Fritzinger et al. |
| 2013/0289564 A1* | 10/2013 | Bernstein ............... A61B 17/82 606/74 |
| 2013/0296930 A1 | 11/2013 | Belson et al. |
| 2016/0000483 A1 | 1/2016 | Stone |

OTHER PUBLICATIONS

The United States Patent and Trademark Office; The International Search Report and The Written Opinion of the International Searching Authority, or the Declaration; International Search Report and the Written Opinion for PCT/US14/11187; dated Apr. 4, 2014; pp. 1-11; The United States Patent and Trademark Office as searching authority; U.S.

The United States Patent and Trademark Office; The International Search Report and The Written Opinion of the International Searching Authority, or the Declaration; International Search Report and the Written Opinion for PCT/US14/015875; dated May 6, 2014; pp. 1-13 The United States Patent and Trademark Office as searching authority; U.S.

* cited by examiner

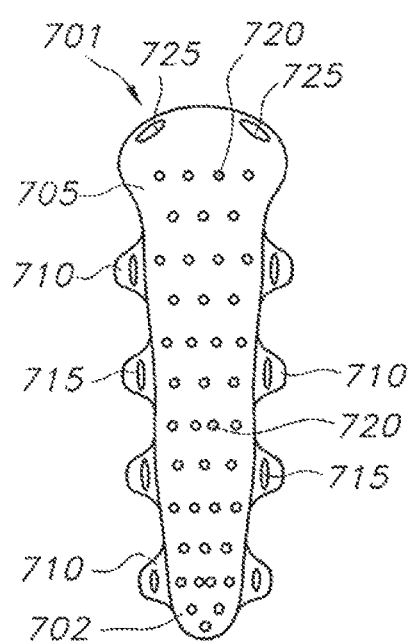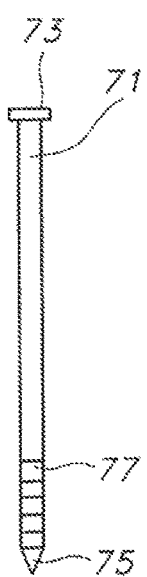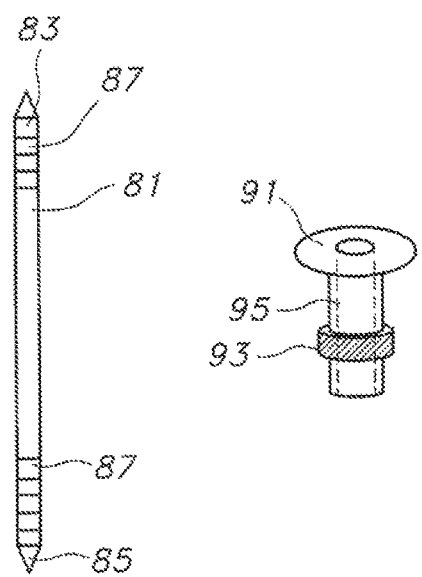
FIG. 8   FIG. 9   FIG.10   FIG.11

STERNUM FIXATION DEVICE AND METHOD

CROSS-REFERENCE TO RELATED APPLICATION

The present application is filed under 35 U.S.C. § 120 as a divisional application of U.S. Nonprovisional patent application Ser. No. 14/153,019, filed Jan. 11, 2014, which claims priority to U.S. Provisional Patent Application No. 61/751,821, filed on Jan. 12, 2013, the specifications of which are hereby incorporated in their entirety herein.

FIELD OF THE INVENTION

This invention relates to an implantable sternum fixation device to secure and aid in the healing of a fractured sternum.

BACKGROUND OF THE INVENTION

Over the last 30 years Open Reduction Internal Fixation (ORIF) with Rigid Internal Fixation (RIF) has become accepted as the standard of care for treating many types of fractures helping patients painlessly return to pre-injury function earlier and more reliably than conventional treatment methods such as casting, bracing and interosseous or cerclage wiring. In addition, when properly applied RIF improves the reestablishment of pre-fracture anatomical bone alignment promoting more reliable infection free healing. Besides the proven benefits in trauma care, ORIF is an acceptable method of repositioning bones in elective procedures and repairing bones surgically cut or fractured when necessary to gain surgical access to perform a primary procedure. Such is the case in open-heart surgery where the sternum is surgically cut to gain access to cardiovascular structures contained within the chest wall. In such cases the sternum is surgically cut along the midline of the long axis of the bone separating the sternum and the associated rib cage in half sections left and right.

The standard method for reconstructing the surgically cut sternum is the placement of stainless steel wires circumferentially (cerclage) around the sternum segments and compressing together by twisting the wires tight to hold the surgically cut bone ends together approximating the pre-cut anatomical position of the sternum and chest wall. In most cases wire fixation has proven to be a successful and cost effective method of repairing the cut sternum with minimal reports of infection and non-union. The literature describes complication rates (infection and/or non-union) as high as 8%. Patients that incur complications, however, endure significant pain and resolving their issues has proven difficult, time consuming, and expensive.

Patients with certain underlying health issues are predisposed to complications. For instance, perhaps most significantly, certain cardiovascular patients with multiple health issues including, as examples, COPD, diabetes, and/or suppressed immune response that may delay or prevent healing, exhibit a propensity for post-operative infection, hardware failure and/or nonunion of the sternum. Other factors, such as age, poor diet, smoking, alcohol abuse and/or drug use, can also adversely affect healing. Many of these patients exhibit diseased bone that is weak and may lack cortical density and thickness.

Over the years, numerous attempts have been made improve a method for fixing the sternum, but most devices are designed to address the sternum after complications have arisen and are not intended to prevent complications by providing an improved primary solution. Furthermore, many of the commonly marketed products tend to be over engineered, complicated and time-consuming to implant. There are also a host of devices that do not appropriately address the complexities of the human anatomy and the demands such fixation must address in clinical applications. Those devices tend to offer no benefit over wire fixation and may lead to unexpected and unintended complications beyond what is known from wire fixation.

The sternum is a flat bone with a thin outer cortex (dense outer bone layer). Cortical density and thickness are important with screw fixation techniques as they provide resistance against pullout when screws are tightened as purchase is achieved by the threads compacting and resting in bone. Cortical density and thickness are also important factors in cerclage wire fixation as stability relies on wires compressing against the cortex to maintain secure fixation.

An implant construct must provide and maintain sufficient stabilization for a duration long enough to allow bone healing to occur. If healing does not occur within an acceptable timeframe hardware loosening often leading to hardware failure becomes an increasing risk. This principle also applies to sternum fixation. In the patient population prone to delayed healing and increased risk of complication, cerclage wire fixation may be contraindicated. In such cases, failure occurs due to broken or loosened wires. In some instances, such wire(s) loosens by cutting through the sternum cortex (commonly referred to as the "cheese grater effect"), which leads to mobility of the bone fragments, potential fracture of the sternum, and almost certain infection. Frequently when patients exhibit failed cerclage wire fixation, radical debridement of soft tissue and bone is necessary and reconstruction resembles more of a salvage mission.

Coughing, which is a very common post-operative occurrence, especially with patients with COPD or pneumonia, can cause high tensile forces on the repaired sternum, thus increasing the rate of failure of cerclage wire, as well.

Uncontrolled motion between two fractured bone fragments may also contribute an increased incidence for infection. As such, the fixation construct chosen must control motion under functional loading conditions to create a favorable healing situation. Opinions have varied over the years as to how much rigidity is desirable in a fixation construct. Historically, it was considered a treatment goal to create a motion-free interface between two bone fragments which was achieved by compressing the fractured or severed bone surfaces in direct opposition, eliminating all motion and encouraging direct healing without the formation of a callus. However, it has now been realized, through the passage of time and the gaining of valuable experience in this area, that the need for extreme rigidity, and thus the elimination of all motion in this situation, is not necessary nor the prevention of callus formation. In essence, it has been found that fixation constructs that are substantially more rigid than the bones they are holding can lead to a condition known as stress shielding that fosters poor bone quality and strength of healed bone and giving rise to potential secondary complications. Excessively strong implant constructs can also create stress risers that predispose bone to potential fracture or re-fracture. Load-sharing by implants is increasingly gaining favor as it is thought to promote healthier and stronger bone.

Another consideration is whether fixation implants can and should be left in the body long-term or permanently. There are many factors to consider such as patient age, the anatomical location of the implant, and the difficulty in removal. Generally, however, most surgeons prefer to leave fixation implants in vivo permanently and not perform a secondary procedure for removal whenever possible. Many cases of fixation implant removal result from patient complaints of discomfort, irritation, and palpability. An ideal implant design is one that can be left in permanently and causes little or no pain or discomfort to the patient during the healing phase and beyond.

The implant material is another major consideration in making the best implant fixation choice. It is vitally important (for clear reasons) that the implant be biologically stable and not cause irritation or another undesirable reaction while in the body. Furthermore, consideration should be given to an implant's potential effect on diagnostic, imaging, monitoring and other therapeutic technologies necessary to care for post-operative patient care.

The speed and ease of installation are important considerations to make when choosing an implant fixation construct. Cardiovascular surgeons are not orthopedists and therefore not routinely familiar with drills, screwdrivers and other "bone carpentry" tools. Many sternum closure devices currently offered require such items as they are based on orthopaedic plate and screw technology. These devices typically require multiple instruments, have many individual parts, and take an excessive amount of time to install adding additional time and cost to the surgery.

The speed and ease of implant removal are also critical factors when choosing a fixation implant construct, especially in the case of a target sternum whereby emergency surgical re-access may be required should the patient incur a life-threatening health event necessitating surgical reentry of the chest wall. If a device requires special instruments to remove or has become biologically imbedded in the soft tissues and/or bone, valuable time can be lost dealing with locating removal instrumentation and exposing and removing the implants.

Additionally, the cost of an implant device construct must be reasonable and not add significantly to the overall cost of performing surgery. In the case of the sternum cerclage wire fixation, the material cost of surgical wire is insignificant. Plate and screw constructs for sternal closure range in price but easily can cost $3,000 to $5,000 per device. In addition, there are disposable components, such as drill bits, etc., that add to the cost of surgery. Most sternum-plating sets are configured as reusable trays containing an assortment of implants and reusable instruments requiring sterilization, cleaning, and restocking between each use requiring additional costs and labor.

Current sternal fixation devices include rigid-plate solutions with elaborate locking screws (where the screws simultaneously thread into the plate and sternum). Implants, such as those available from Synthes, comprise of two or three of the plates consisting of left and right segments joined together by a quick release "grenade" pin mechanism. These plates are spaced and implanted along the anterior facing sternal surface midline straddling the saw cut with screws inserted into the sternum on both sides of the cut. If emergency re-access becomes necessary, the operator must remove the pins and separate the sternum and associated rib attachments left and right giving immediate access through the chest wall. Uncoupling the plate only uncouples the bone when the bone remains unhealed. If reentry is attempted after the soft tissue and bones have healed, simply removing a pin will not provide immediate re-access. Further complicating access during revision surgery is the positioning of the bulky metal implant directly over the desired placement for the saw cut needed to open a partially or fully healed sternum. Such screw-secured implants are also very time-consuming to implant and costly to produce. Their excessively rigid construction results in stress-shielding and detrimental bone loss and possibly delayed and or poor healing.

In another variation of a prior device, reduced stress shielding has been provided through the utilization of braided cables through sterna-positioned cannulated metallic grommets. Unfortunately, though, this alternative still requires excessive operating time and a skill-dependent implantation procedure. The cable is laced along the sternum like laces on a shoe and tightened with a special cable crimping instrument. The process for installation is too cumbersome and time consuming and getting the bone segments back into anatomical position has proven too difficult for widespread, reliable use.

Self locking ties, similar to "zip ties" placed around the sternum through the intercostal spaces of the sternum provide an improvement in simplicity, however, provide no better fracture immobilization than cerclage wire. The zip-tie fixation method disregards the significant forces loaded on the sternum and is not an adequate solution for, in particular, at-risk patients. Therefore, locking ties only appear to offer a potentially more convenient way to achieve the same benefits as cerclage wiring and may contribute to complications resulting from unsatisfactory mechanical characteristics when used in such an application.

Other devices attempting to solve the sternal closure method include a mechanical clamp that cleats around the sternum passing through the intercostal spaces. When used in series, these metallic clamps compress the sternum together. The clamps are large, excessively rigid and frequently uncomfortable and irritating to the patient frequently necessitating post-operative removal, as well as comparatively costly.

The other identified competitive offerings seem to follow a plate-and-screw approach to fixing the sternum, typically with cuttable struts across the central section facilitating removal. None of them appear to offer significant benefits over each one another. Due to the significant forces that act on the sternum under normal and extreme functional loading all present similar risks of post-operative complication.

A need thus exists for an inexpensive, implantable, load-sharing sternal fixation device that is easy to implant, minimizes disruption to the surrounding soft tissues, and that allows simple removal to re-access to the chest cavity by conventional methods. To date, the sternum fixation industry has yet to provide such a beneficial alternative to the current devices described above.

BRIEF SUMMARY OF THE INVENTION

The invention disclosed involves a novel method referred herein as "circumfixation" device and method. This novel approach to fixation achieves a better fixation construct than previously available for a variety of clinical indications. In the case of sternum closure fixation, circumfixation device, and method represents the perfect choice as it precisely addresses the prerequisites of sufficient rigidity, ease of application and removal, biologically stable, well-tolerated, non-obstructive to other diagnostic and therapeutic technologies while remaining cost beneficial.

The inventive sternum circumfixation device and method can be best described as a type of internal splinting utilizing at least one specially designed plate-like body and a plurality of corresponding strap-like fastening members, herein also referred to as "s locking fasteners." The body, herein also referred to as a "plate," is shaped to generally resemble the sternal body to be placed along its surface and secured in position by the use of zip tie-like locking fasteners that pass behind the sternum through the intercostal spaces and lock to the plate through special locking slots incorporated into the plate. The ideal material composition is a thermoplastic polymer such as polyether ether ketone (PEEK) because of its high strength and stiffness that can mimic human bone and its ability to be adapted to the irregular surface of the sternum and its high fatigue strength that permits prolonged load sharing throughout a delayed healing response. The material allows the plate to be made low profile and more closely replicate the strength and elasticity of the human sternum while being completely biologically compatible and well tolerated by the patient. A large singular plate allows for better anatomical restoration and is necessary to counteract the tensile, torsion and shear forces acting along the forward facing surface of the sternum. The use of fasteners instead of screws creates not only a safer fixation construct, together with the plate they allow for load sharing and promote micro movement thought to be beneficial to healthy bone healing. In addition, fasteners can be applied quickly with minimal instrumentation and easily removed with nothing more than surgical scissors. Furthermore, whereas screws rely on healthy dense bone for the threads to maintain their grip, sternum bone has been shown to have poor cortical density and thickness that may not be sufficient to prevent screw strip out under the extreme loads common to the sternum under normal physiological function, the invention places the loading over a larger surface area of cortical bone.

Circumfixation provides the additional advantage of providing a biomechanical and biological approach to bone healing. It is appropriately termed "biomechanical" because this method considers not just the forces acting on the bone but the fundamental purpose of the bone itself. The fixation allows the bone to function in the manner it was intended while maintaining it sufficiently stable to achieve desirable and predictable healing. The term "biologic" applies because it mimics the strength, stiffness, and elasticity of the target bone while allowing the body's natural healing abilities to take effect. While spanning the sternum, the circumfixator plate rests on torsion rails that minimize direct contact with the bone surface thus promoting the free flow of fluids and cellular activity at the healing site. Furthermore, the inert nature of the implant does not retard or interfere with desirable healing. It also avoids unnecessary trauma to bone that results from drilling and placing foreign bodies therein (such as screws and/or cables, as non-limiting examples). The sternum circumfixation construct applies desirable compression along the entire bone fragment interface which enhances healing while controlling the range of dynamic forces acting on but not eliminating micro-motion thought to be beneficial to the healing process.

The sternum circumfixation construct is also safe and well tolerated by target patients. Unlike plates, screws, and/or clamps, there are no sharp edges or pointed tips that could seriously harm patients if they were to fall or suffer trauma to the sternum region either during the healing phase or after healing is complete. This new device thus also avoids the overly rigid metallic constructs that create stress risers in the surrounding bone. Overall, then, the inventive device further reduces the likelihood of bone fractures that can occur as a result of overloading at the location of the stress riser. As mentioned earlier, many cardiothoracic patients have co-morbidities making them predisposed to infection, to delayed healing, and to poor bone quality and blood perfusion. For these high-risk patients especially, sternum circumfixation is a superior choice as a short term, long term, or permanent implantation period. The flush smooth surface of the sternum circumfixator and fasteners causes no irritation to the surrounding tissues and bone. The lack of metallic components (which are required of all prior sternum repair devices) also reduces the patient's sensitivity to cold temperatures.

Accordingly, the invention thus encompasses herein a plate having two substantially parallel longitudinal sides and two latitudinal ends, wherein said plate is contoured to lie passively against the forward facing aspect of the human sternum when placed directly on its irregular flat surface, wherein said plate includes a plurality of tie fasteners attached to portions of said longitudinal sides and configured to hold said plate on said sternum surface when attached around the under surface of said sternum and tensioned. Furthermore, the invention encompasses such a plate wherein said fasteners are zip tie-like fasteners having attachable cannulated handles for fastener manipulation and tensioning; wherein said plate is constructed from a biocompatible plastic material selected from the group consisting essentially of PEEK, PEAK, PAEK, UHMWPE, Silicone, ULTEM, RADEL, PPO, PPS, Nitinol, Stainless Steel, Titanium alloy, oxidized zirconium, ceramic, cobalt chrome, resorbable polymers, and collagen. The plate may be from 1 to 10 mm in thickness and may exhibit a tapered shape to conform to the general shape of the target sternum. As well, the plate may include a series of spaced slots (holes) numbering between 4 and 6 on either longitudinal side thereof, said slots being situated near the outer edges of said longitudinal sides and being in direct opposition to each other along the longitudinal axis of said plate. Such slots may further be spaced for the purpose of alignment with the intercostal spaces between the ribs at the juncture where they meet the target sternum.

Additionally, such slots may be present on winged tabs incorporated into said plate configuration such that said tabs extend slightly past the sternum and over said intercostal spaces allowing the passage of said fasteners around the posterior aspect of the sternum connecting to the plate on both sides through said slots. These winged tabs may thus be bendable to adapt to the surface of the target patient's bony anatomy when said fasteners are tensioned. Additionally, the plate may be configured in such a manner as to be porous, or, alternatively, may include a plurality of perforated holes therein to allow body fluids to pass through and around said plate (or to hold medicaments therein for delivery within the target patient's chest cavity during utilization). Furthermore, the plate may be either flat or slightly angled upward to adapt to the rise of the target sternum at the junction of the sternum and manubrium. To aid in proper stability, the plate may also include vertical and horizontal torsion rails incorporated within the sternum-contacting surface of said plate.

Overall, then the inventive device may permit a suitable protective/healing method for a target patient by providing a splint to the sternum of a patient subsequent to an open-chest operation wherein said patient's sternum has been severed into two separate open sides, said method comprising the steps of: a) supplying a plate as described above; b) bringing said two separate open sides together to reconnect said severed sternum; c) placing said plate of step "a" onto the anterior surface of said reconnected sternum; d) running said fastener ties from one longitudinal side of said plate around the posterior surface of said reconnected sternum; and e) tensioning said ties to the opposite longitudinal side of said plate.

The invention will be further and more succinctly described below.

BRIEF DESCRIPTION OF THE DRAWINGS

FIG. 8 shows a front view of an embodiment of the invention.

FIG. 9 shows a single ended locking fastener of an embodiment of the invention.

FIG. 10 shows a double ended locking fastener of an embodiment of the invention.

FIG. 11 shows a cannulated tensioning handle of an embodiment of the invention.

DETAILED DESCRIPTION OF THE DRAWINGS AND PREFERRED EMBODIMENTS OF THE INVENTION

Figure 1:
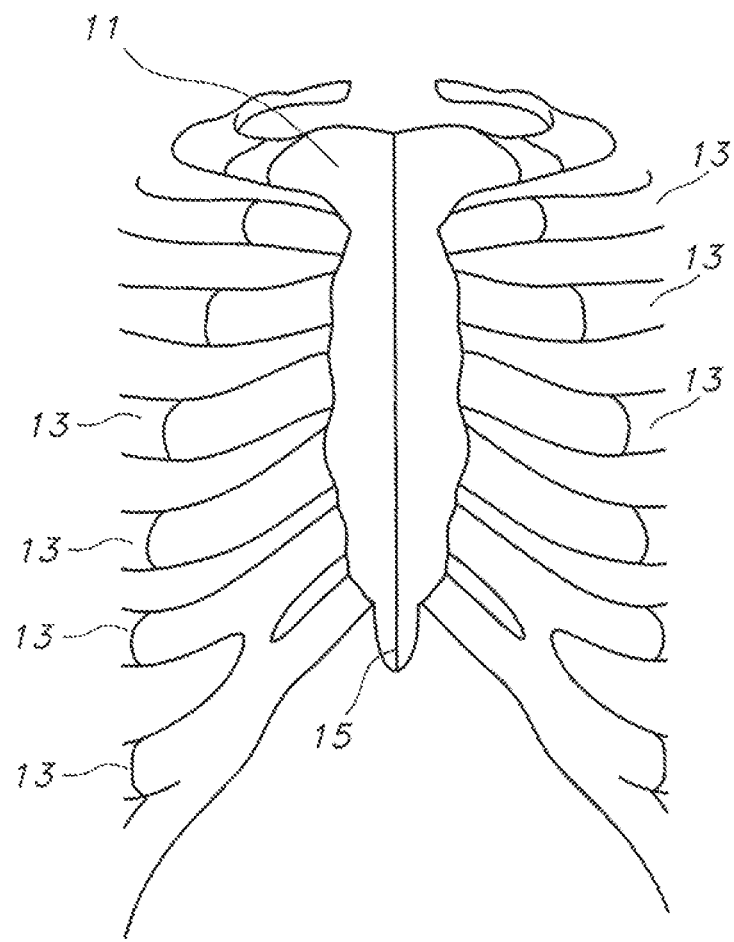
FIG. 1 is a front view of a sternum having a longitudinal cut.

Accordingly, the inventive device thus encompasses a plate contoured to lie passively against the forward facing aspect of the human sternum when placed directly on its irregular flat surface, zip tie-like locking fasteners and attachable cannulated handles for manipulating and tensioning the fasteners. The sternum plate is preferably fabricated from a biocompatible plastic material like polyether ether ketone (PEEK), PEAK, polyaryl ether ketone (PAEK), ultra-high molecular weight polyethylene (UHMWPE), Silicone, polyether imide (such as from ULTEM®), polyphenyl sulfone (such as RADEL® from Solvay), poly(p-phenylene) oxide (PPO), poly(p-phenylene) sulfide (PPS), Nitinol, Stainless Steel, titanium alloy, oxidized zirconium, ceramic, cobalt chrome, resorbable polymers, carbon fiber, carbon fiber reinforced PEEK or collagen.

The sternum plate should also be thin (approximately 1-10 mm thick; more preferably, 1-5 mm), slightly tapered in the shape of a human sternum, and also slightly parabolic (or possibly rectangular) in shape to meet the general dimensions resembled by the human sternum. The plate should have a series of spaced slots (holes) numbering between 4 and 6 (left and right) placed near the outer edges in direct opposition to each other along the long axis of the plate. The slots are spaced for the alignment with the patient's intercostal spaces (the spaces between ribs at the juncture where they meet the sternum). The slots could be placed on winged tabs incorporated into the plate design that extend slightly past the sternum and over the intercostal spaces allowing the easy passage of fasteners around the posterior aspect of the sternum connecting to the plate on both sides through the slots. The winged tabs are preferably bendable to adapt to the surface of the bony anatomy when the fasteners are tensioned, as well. The plate may also potentially preferably be porous or have perforated holes to allow body fluids to pass through and around the plate. The plate is also potentially preferred to be flat or slightly angled upward to adapt to the human sternum that tends to rise at the junction of the sternum and manubrium. The plate may also be configured to potentially preferably incorporate vertical and horizontal "torsion rails" incorporated into the bone facing aspect or undersurface of the plate. Such a feature would reinforce the strut plate while maintaining an ultra low profile when in place on the target sternum. In addition, such a feature would limit contact on the bone surface allowing the free movement of bodily fluids under the plate promoting biological healing.

The fasteners potentially preferably resemble zip ties in appearance. Unlike zip ties, however, the fasteners will lock through corresponding "female" slots incorporated in the plates with each slot containing a locking mechanism that prevents the fasteners from backing out after the ends are threaded through slots. There are two major types of fasteners: single-ended locking and double-ended locking. The single-ended locking fastener (SELF) has a head on one end that prevents it from pulling through a non-locking slot and has a textured surface on the opposite end that allows it to mesh with the locking mechanism contained in the corresponding locking slot preventing it from backing out when tensioned. The second type of fastener would be the double-ended locking fastener (DELF) whereby both ends of the fastener can be locked through slots containing locking mechanisms. All types of fasteners could have a cardiac needle affixed to one of the male ends. The use of cardiac needles will allow the operator to easily pass the attached fasteners through the soft tissue, muscle and cartilage adjacent to and surrounding the sternum. The fasteners are placed behind the sternum and emerge through the intercostal spaces on both sides of the sternum and attach to the plate by threading through the slots. After the leading end or male end of the fastener is introduced and completely passed around the sternum the needle portion can be removed and the remaining tip can be passed through a female slot with a locking mechanism, allowing the fastener to be tensioned pulling the sternum fragments closed. Once the chest wall is sufficiently closed, the excess fastener end can be trimmed back and removed leaving the fastener flush at the surface of the locking slot. Alternatively, a special cannulated awl could be used to tunnel under and around the sternum easing the passage of fasteners without the use of cardiac needles.

The cannulated tensioning handle can be temporarily attached and used to tension the fasteners to enable closure of the open sternum. This is accomplished by engaging the ends of the fasteners with the handle so that the handles can be pulled with human power to provide tension on the fasteners pulling against the plate while closing the sternum. After tensioning, the handles can be released from the fasteners and the handles can be disposed.

The sternum plate covers the sternum body and manubrium and is affixed to the bony anatomy with the aforementioned zip tie-like strap fasteners that pass behind the sternum and lock to the strut plate that is placed on the forward facing aspect of the sternum and manubrium. When secured in place the device assembly supports and holds the surgically cut bones and their attachments in anatomical approximation effectively closing the chest wall by compressing together along the cut or fractured bone surfaces thereby effectively reducing the pain typically associated therewith (or even promoting pain-free healing overall) of the sternum and surrounding tissues while at the same time allowing the flexibility for the chest cavity to expand and contract during breathing, coughing, and/or other physiological loading. The fasteners interact with the sternum plate by attaching to it through the slots and compressing the device assembly around the bony fragments when tensioned bringing the surgically cut bone ends into direct contact to promote biological healing with bony union.

Thus, the inventive device encompasses, in one potentially preferred embodiment, an implantable medical device used to repair and reconstruct the human sternum (breast bone) following various open-chest cardiac surgical procedures including thoracotomies, CABG, as well as other unnamed open-chest procedures necessitating surgical cutting of the sternum to gain access to the internal chest cavity. Typically, the necessary surgical cut is made in the sagittal plane along the midline of the sternum longitudinally, allowing the separation of the sternum and rib cage attachments (to the left and the right). The device is to be implanted at the time of closure allowing the separated segments to be anatomically re-approximated and compressed together to promote bony union and healing of the surrounding soft tissues while reducing or eliminating pain, infection and potential of non-union. It could also be used to repair and reconstruct the chest wall following traumatic injury sustained as a result of fracture(s) to the relative bony structures.

The potentially preferred device encompasses a plate that is placed over the sternum and is secured in position in a splint-like fashion with a series of zip tie-like fasteners passed behind the sternum through the intercostal spaces and attached and secured to the plate through corresponding slots (holes) in the plate with some or all incorporating a locking mechanism which grips and locks around the rib textured surface of the fastener ends. When sufficiently tightened, the plate and fastener assembly compresses the plate, fasteners, and (any resultant) bony fragments snugly together in anatomical position reducing pain and promoting postoperative healing of the bone and surrounding tissues. This action of fixation modality is referred to as "circumfixation" herein.

The fastening devices utilized herein for the circumfixation method could be locking or passive (non-locking). A single-ended fastener could have a head at one end that stops and rests flush when it meets the surface of the plate after it is threaded through a non-locking slot and tensioned when the locking end of the fastener is passed through the corresponding or opposing locking slot on the contralateral side of the plate and tensioned. The distal end of the fastener will lock after threading through the distal plate slot and being tensioned thereafter. A double-ended fastener, whereby both ends offer the capacity to be simultaneously tensioned and locked through opposing plate slots, could be beneficial to achieving even tensioning of the construct, as well. The surface geometry of the potentially preferred fasteners could be of any shape, although for simplicity sake, square or rounded would be potentially preferred, too. A rounded surface, in particular, might be beneficial as it might be less of an irritant to the bone and adjacent soft tissues under tension and mechanical load. The fasteners could also be cannulated allowing their passage over a guide wire to aid in their passage through muscle and tissues and during placement. The fasteners might include a cardiac needle on one end allowing their passage through soft tissue, muscle and cartilage found around the sternum. After tunneling through the soft tissue, muscle and/or cartilage, the cardiac needle can be severed from the fastener and discarded. Cannulated handles could be temporarily attached to the fastener ends once they are threaded through opposing plate slots, allowing the operator a means for tensioning the fasteners in position by pulling on the handles. Such potentially preferred cannulated handles could be made from metal or plastic and could include, if desired, a threaded nut/ring around their barrels that when tightened reduces the cannulation aperture, allowing them to attach to fastener ends for tensioning and manipulation. Upon un-tightening (actively loosening, in other words) of the threaded nut/ring, the handle can thus be easily removed. Such cannulated handles could thus be utilized in association with single- or double-ended locking fasteners. By pulling on such cannulated handles attached to the fastener ends, the device assembly surrounding the bone fragments can be manipulated allowing the bone fragments to be moved into proper anatomical position and securing the device assembly in position by compressing the plate and fasteners around them.

The plate and fastener assembly must be sufficiently strong to withstand the biomechanical forces typical under normal and severe functional loading conditions. The implant material should be biocompatible, light-weight, radiolucent, and easily removable should emergency surgical re-entry through the chest wall be necessary. An ideal method of removal would be the ability to release the fixation with a common pair of surgical scissors by cutting through the fasteners allowing the plate and fasteners to be quickly and easily removed.

In essence, the basic advantage of this invention is to provide an improved implantable medical device and technique to repair and heal a surgically cut or fractured sternum and surrounding soft tissues in an effort to restore preoperative anatomical form and function and bony union though healing. The plate is thought to be semi-rigid allowing for flexing of the thorax during breathing, coughing and other physiological movements while maintaining anatomical positioning of the bony fragments during the healing phase. The device assembly is intended to be easily applied and removed if emergency re-access is indicated. The device is intended to reduce post-operative pain and infection and to be biocompatible, allowing it to remain in the body permanently. The device is also intended to be inert and radiolucent causing no interference with any testing, diagnostic or imaging technology applied to the patient postoperatively.

Many cardiac surgical procedures require passage through the chest wall to access the vital organs contained in the inner cavity. Surgical assess is typically gained by cutting the sternum in half with a surgical saw along its long access (median sternotomy) allowing the separation of the chest wall and rig cage left and right. A sternum closure device is designed to reduce and maintain the chest wall in anatomical position following such open-chest procedures in which a median sternotomy was performed. There are numerous competing devices and techniques already in use for closing the sternum. The "gold standard" is cerclage wire which is adequate in most surgeries. However, as discussed above, such wire implements are time-consuming to apply and the operator risks puncture resulting in exposure to potential pathogens and contractible diseases harbored by the patient. Wire fixation alone does not provide much stability and can loosen or break over time, particularly if the patient has other compromised underlying health conditions (e.g., timely healing is not highly predictable). Patients with certain underlying diseases such as COPD, diabetes, osteoporosis and alcoholism are more likely to have delayed and/or complicated healing. Older patients or patients that smoke are also candidates for delayed and/or complicated healing. For these high-risk patients, cerclage wiring is often insufficient fixation for closing the chest wall. In such instances, wire hardware frequently loses the race against time, exhibiting undesirable loosening or breakage before bone healing has been achieved. In such cases of failure, infection is a frequent complication which can lead to serious consequences requiring multiple surgical procedures to resolve and cause significant pain and discomfort to the patient.

Other methods include the use of metal plates that are fixed with screws to the sternum and rib cage. These plating constructs are usually too rigid for the purpose for which they are intended and the potential for screw loosening or strippage in the weak bone and cartilage is of concern. They are also costly and time consuming to apply and pose potential risks and complications post-operatively. Another marketed device is a metallic clamp that secures around the sternum by compressing along the long axis when applied as a series of clamps. The clamps have feet placed in opposing intercostal spaces and joined together with an interlocking mechanism that tightens by ratcheting. Such clamps are generally highly engineered, extremely rigid, difficult to apply and expensive. Their stiffness could interfere with a patient's physiological functioning by preventing the chest from expanding and contracting during breathing, coughing and other normal physiological movements which could compromise healing. Other methods involve the use of zip ties made from PEEK material that wrap around and under the sternum much like the cerclage wire technique but instead of tying closed use a zip tie closure mechanism to cinch shut. Both the cerclage wire and the zip-tie method (on its own) pose significant risks to patients through the propensity of such materials irritating and/or cutting through the sternum due to high stresses during coughing and breathing and do not provide enough stability to maintain anatomical alignment and ensure reliable healing in the high risk patient population. Such problems are overcome through the utilization of the inventive sternum splint device.

Additionally, the proposed invention could be designed to elude therapeutic agents such as antimicrobials and/or bone healing agents like stem cells or BMPs. Alternatively, the device could be coated with said agents to promote infection free healing. The device could also be embedded with smart technology to perform various diagnostic and/or clinical tasks or provide dockage for other implantable technologies.

The invention thus encompasses a rigid or semi-rigid plate in the general shape of the human sternum that is placed over the sternum for the purpose of splinting the sternum into position for healing following a surgical cut to the sternum separating it into left and right halves longitudinally technically described as sternotomy. The device might also be applied to secure the sternum in position following traumatic injury resulting in fracture. The plate has spaced slots along the lateral edges of the plate to accommodate the placement of fastener straps that are passed behind the sternum and threaded through opposing slots. Some or all of the slots can be configured with a locking mechanism that allows the fasteners to be fixed to the plate when tensioned. The slots are spaced to overlay the gaps between ribs known as intercostal spaces allowing for the fasteners and plate to circumferentially surround the sternum and hold it in secure position to promote reduced pain or pain free bone and soft tissue healing mitigating many potential complications observed with conventional methods. The plate might be configured with rigid or bendable flaps or wings with the slots located within to facilitate simplified placement of the fasteners. Due to anatomical differences of different statured patients, it might be necessary to offer multiple sizes of plates to properly conform to the target person.

The plate might also be configured with a capability to deliver therapeutic agents, as noted above, such as antibiotics, pain control medicines, cancer treatments, bone-healing growth factors such as stem cells, BMPs, and the like. The plate might also be coated with antibiotics or bone healing agents to allow for delivery to the patient.

Circumfixation could also have applications in rib fracture fixation, clavicle fracture fixation, wrist bracing and/or reconstruction, ankle bracing and/or reconstruction, spinal bracing and/or reconstruction and possibly other unidentified applications, with the device configured to at least some portion of the patient's bone and a suitable manner of wrapping and connecting ties, and the like, around the target bone (as for the sternum splint described herein).

Without any intention of setting limitations on the breadth of the invention described herein and encompassed within the accompanying claims, herein provided are descriptions of drawings of the non-limiting preferred embodiments of the inventive device.

FIG. 1 shows a frontal view of the sternum 11 and a plurality of ribs 13. Typically a cut 15 is made in the sagittal plane along the midline of the sternum 11 longitudinally allowing the separation of the sternum 11 and rib cage attachments left and right. The device is to be implanted at the time of closure allowing the separated segments of the sternum 11 to be anatomically re-approximated and compressed together to promote bony union and healing of the surrounding soft tissues while reducing or eliminating pain, infection and potential of non-union. The invention could also be used to repair and reconstruct the chest wall following traumatic injury sustained as a result of fracture(s) to the relative bony structures. This FIG. 1 thus merely shows the prior art situation of a surgically cut sternum in need of some type of connection to promote healing.

Figure 2:
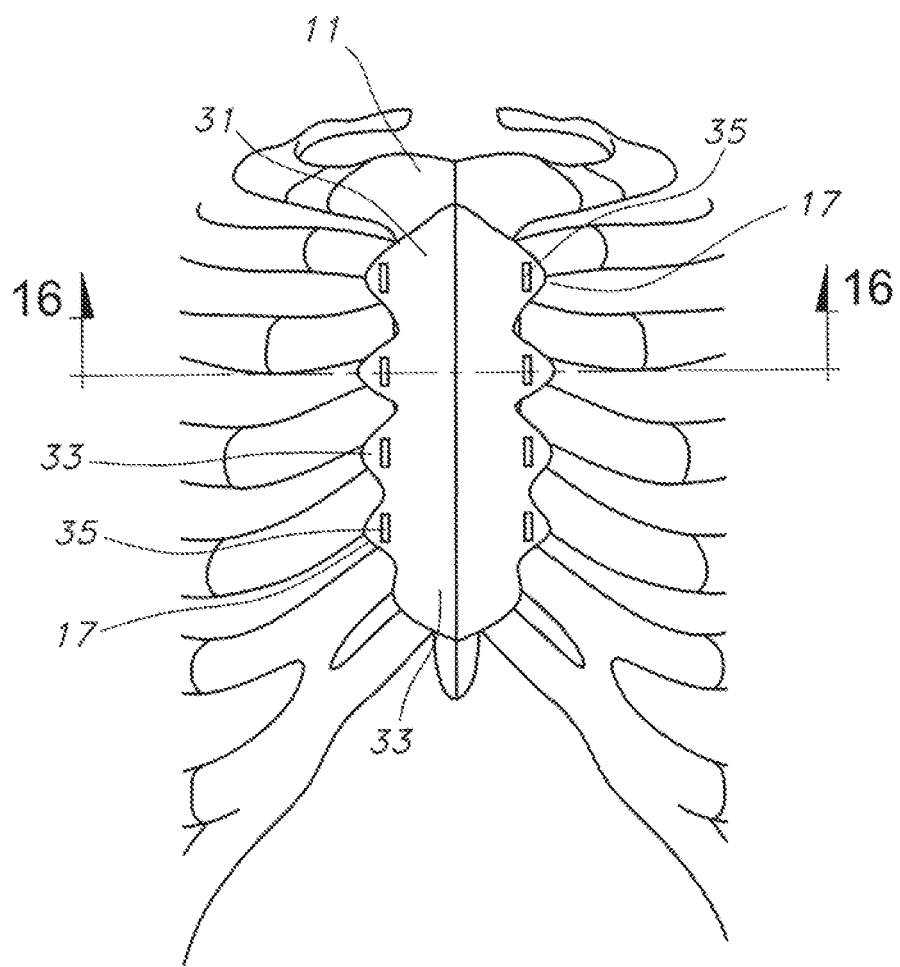
FIG. 2 is a front view of a first embodiment of the invention.

FIG. 2 thus shows a first embodiment of the invention 31 comprises a plate 33 that is placed over the sternum 11 and is secured in position in a splint-like fashion with a plurality of self locking fasteners, such as zip ties, passed behind the sternum 11 through the intercostal spaces 17 and attached and secured to the plate 33 through corresponding slots (also referred herein as holes or apertures) 35 in the plate 33 with some or all incorporating a locking mechanism which grips and locks around the ribbed textured surface of the fastener ends. When sufficiently tightened the plate and fastener assembly compresses the plate, fasteners and the bony fragments snugly together in anatomical position reducing pain and promoting postoperative healing of the bone and surrounding tissues. As noted above, this fixation modality is described herein as "circumfixation."

Figures 3A, 3B:
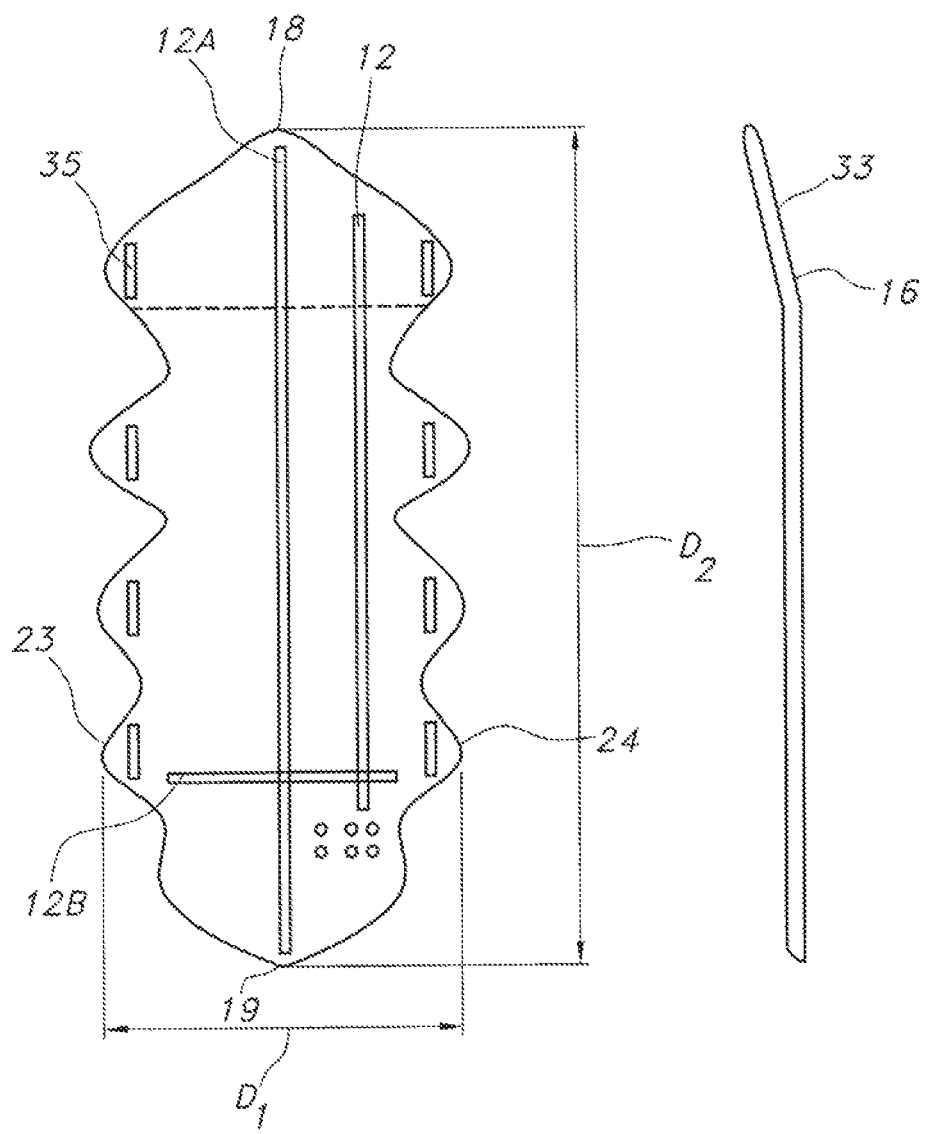
FIG. 3A is a rear view of the invention showing partially formed torsion rails and perforations.
FIG. 3B shows a right side view of the invention.

FIG. 3A shows a rear view of the first embodiment of the invention, showing a plurality of torsion rails which stiffen the plate while providing reduced surface area contact with the underlying bone.

FIG. 3B shows a side view of the first embodiment of the invention.

Figure 4:
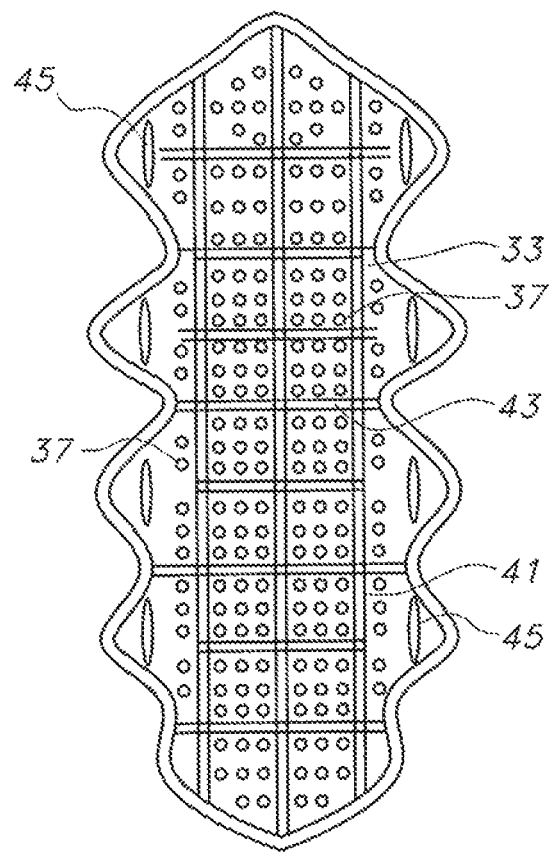
FIG. 4 shows a rear view of the invention showing.

FIG. 4 shows a rear view of the first embodiment of the invention 31, showing a plurality of perforations 37 though the plate body 33, torsion rails 41, 43 and apertures 45 through which fasteners may pass.

Figure 5:
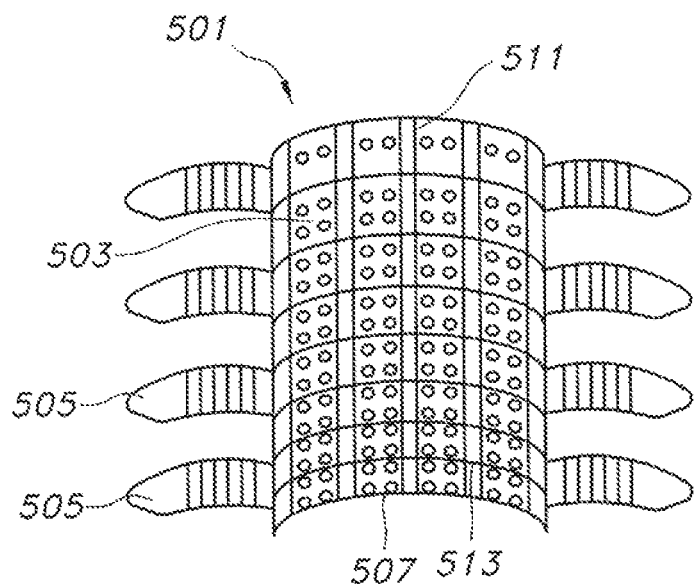
FIG. 5 shows a rear view of the male plate portion of a second embodiment of the invention.
Figure 6:
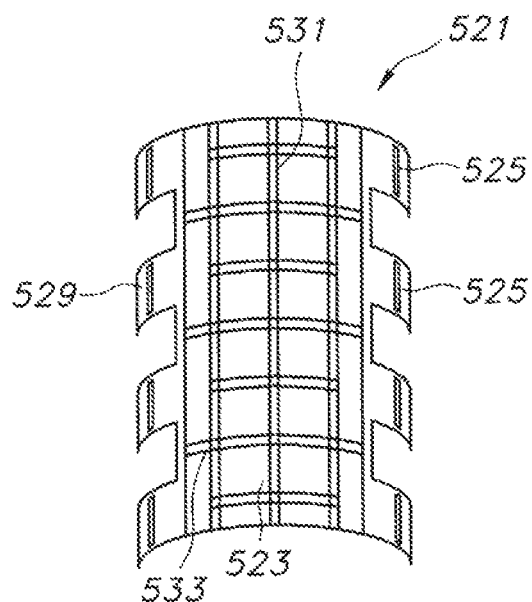
FIG. 6 shows a rear view of the female plate portion of a second embodiment of the invention.

FIGS. 5 and 6 show a dual plate embodiment having a male plate 501 and a female plate 521. The male construct 501 possesses a plurality of fastener straps 505 extending from the plate body 503. In this particular embodiment, the male plate body 503 possesses a plurality of apertures 507 allowing the passage of fluids through the plate. The plate body 503 also possesses a plurality of elongated protrusions or "torsion rails" 511 running up and down as well as a plurality of torsion rails 513 running across the body 503. The female construct 521 possesses a plurality of torsion rails 533 and 531 which increase the plate body 523 rigidity and reduce the total contact surface area with the tissue being secured by the plate. A plurality of apertures 525, each possessing a self locking mechanism receive the male fasteners 505 of the male construct plate construct 501. The apertures 525 are be positioned, preferably, out on protruding sections or wings 529 of the body 523.

This type of circumfixation is referred to as circumfixation method "type B." Whereas the first embodiment and method described the use of a plate and multiple independent locking fasteners to create a fixation construct, the "type B" method does not employ independent locking fasteners, rather, the fastening feature is incorporated into the plate body geometry 503, 523 resembling phalanges extending from the body of the plate. Locking phalanges 505 extending from the body of the plate herein referred to as "male" plate body are joined to a second plate body with corresponding locking slots 525 designed to accept and secure around the profile of the locking phalange fastener ends herein referred to as "female" plate body when they are inserted through the locking corresponding locking slots. The size, shape, thickness, strength, stiffness and material composition of "type B" circumfixator plate bodies and the quantity, size, strength and flexibility of the locking phalanges and receptor locking slots will vary depending on a number of factors including the intended purpose, anatomical location; the size shape, quality and quantity of the bone, bone segments and fragments, etc.

Such a construct might be favorable for fixing or splinting bones round or tubular in shape, including ribs, the spine, femur, tibia, fibula, radius, ulna, humerus, carpels, metacarpals, phalanges, tarsals, metatarsals, clavicle, and the like. Such a construct might also prove ideal for fixing or splinting periprosthetic fractures, various pediatric fractures and osteotomies, and fixing and/or splinting in or over joint areas including the hip, knee, ankle, wrist, elbow, shoulder, spine, fingers and toes.

Figure 7:
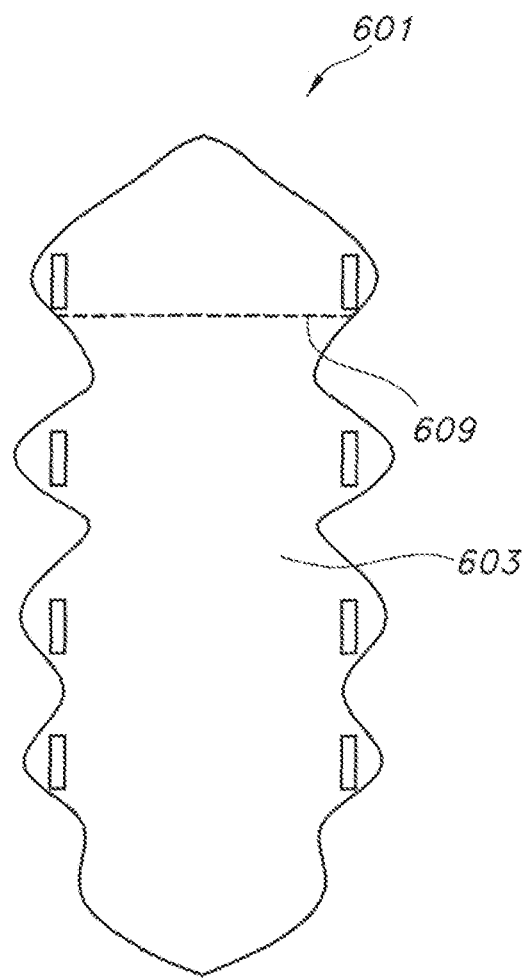
FIG. 7 shows a front view of the invention having a contour transition on its underlying surface to conform at the sternal angle being the junction of the sternal body and manubrium.

FIG. 7 shows another embodiment 601 of the invention possessing no torsion rails. This version possesses a thinned horizontal section 609 allowing flexion of the sternum plate 603 along the sternum and manubrium border.

Fasteners 71, 83 could have single ended locking capability as shown in FIG. 9 or a double ended locking capability as shown in FIG. 10. Likewise plate slots could be locking or passive (non-locking). Under such a scenario whereby the slots incorporated into the plate are passive and do not contain the locking mechanism necessary to lock around the fastener profile, a special locking nut or "donut" could be utilized to achieve the same purpose. A locking nut is slipped over a fastener that has been inserted through a passive plate slot and slipped down around the fastener profile until it meets the plate surface at the junction where the fastener 711 and the passive plate slot 703 intersect. The locking nut would contain a locking mechanism allowing it to grip around the profile of the fastener and prevent the fastener from backing through the slot. The fastener could be tensioned by advancing it through the slot and locking nut allowing for a snug and secure closure. After final tensioning, the excess fastener body would be trimmed and removed just above the top of the locking fastener where the fastener body exits the locking nut.

A single-ended fastener could have a head 73 at one end that stops and rests flush when it meets the surface of the plate after it is threaded through a non-locking slot and tensioned when the locking end of the fastener is passed through the corresponding or opposing locking slot on the contralateral side of the plate and thereafter tensioned. The distal end 75 of the fastener will lock after threading through the distal plate slot and thereafter tensioned. A double-ended fastener 81, whereby both ends offer the capacity to be simultaneously tensioned and locked through opposing plate locking slots, could be beneficial to achieving even tensioning of an implant construct. This would apply to plate slots containing a locking mechanism or passive slots and the use of locking nuts. The surface geometry of the fasteners could be square, as shown in FIG. 21A, rectangular (flat), or rounded as shown in FIG. 21B. A rounded or hexagonal surface may possess less of a potential to irritate the bone and adjacent soft tissues under tension and physiological loading. All potential fastener geometries are better able to evenly distribute their forces across a larger surface area compared to wire which should reduce the potential for irritation and infection. Fasteners may also be cannulated allowing the insertion of a guide wire through their core to facilitate their passage through soft tissues, muscle and cartilage encountered around the sternum at the time of placement. Alternatively, fasteners might incorporate a cardiac needle affixed on one end to aid in their passage through soft tissue, muscle, and cartilage found around the sternum. After tunneling through the soft tissue, muscle and/or cartilage the cardiac needle can be severed from the fastener and discarded.

Cannulated handles 91 as shown in FIG. 11 could be temporarily attached to the fastener ends 75, 83 or 85 once they are threaded through opposing plate slots giving the operator a means of tensioning the fasteners in position by pulling on the handles. Cannulated handles 91 could be made of metal or plastic and might have a threaded nut/ring 93 around their barrel 95 that when tightened reduces the cannulation aperture allowing them to attach to fastener ends for tensioning and manipulation. Upon untightening (or loosening) of the threaded nut/ring the handle can be easily removed. Cannulated handles could be used on single- or double-ended locking fasteners also with or without the use of locking nuts. By pulling on cannulated handles attached to the fastener ends the device assembly surrounding, the bone fragments can be manipulated allowing the bone fragments to be reduced into anatomical position and securing the device assembly in position by compressing the plate and fasteners around the bony fragments.

The plate and fastener assembly must be sufficiently strong to withstand the biomechanical forces typical under normal and severe functional loading conditions. In the preferred embodiment, the implant material would be biocompatible, light-weight, radiolucent and easily removable should emergency surgical re-entry through the chest wall be necessary. An ideal method of removal would be the ability to release the fixation with a common pair of surgical scissors by cutting through the fasteners allowing the plate and fasteners to be quickly and easily removed.

Figure 12:
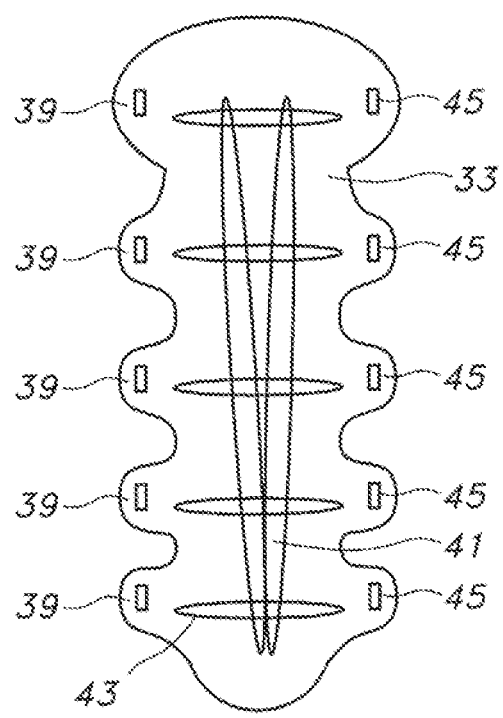
FIG. 12 shows a rear view of an embodiment of the invention.

As shown in FIG. 12, the plate 33 may be configured with rigid or bendable flaps or wings 39 with the slots located within to facilitate simplified placement of the fasteners. Due to anatomical differences of different statured patients it might be necessary to offer multiple sizes of plates to properly conform to the variable anatomy.

Preferably the fasteners have a rack of ridges resembling zip-ties. In the preferred embodiment the fasteners could lock through corresponding "female" slots incorporated in the plates 33 each slot containing a locking mechanism that prevent the fasteners from backing out after the ends are threaded through slots. Alternatively, fasteners could be secured with locking nuts that each contain a locking mechanism and secure the fasteners in position when advanced along the outer profile of fasteners once they have been passed through passive or non-locking plate slots and firmly pressed up against the plate slot interface restricting the fastener from backing through the plate slot. There are two major types of fasteners: single ended locking and double-ended locking. FIG. 9 shows the single ended locking fastener (SELF) 71 which has a head 73 on one end that prevents it from pulling through a non-locking slot and has a textured surface 77 on the opposite end 75 that allows it to mesh with the locking mechanism contained in the corresponding locking slot preventing it from backing out when tensioned. The second type of fastener would be the double ended locking fastener (DELF) 81 whereby both ends of the fastener 83, 85 can be locked through slots containing locking mechanisms. In an alternative embodiment of either type of fastener, the fastener has a cardiac needle fused to one of the male ends through a molded in process or suture tie. The use of cardiac needles will allow the operator to easily pass the attached fasteners through the soft tissue, muscle and cartilage adjacent to and surrounding the sternum. The fasteners are placed behind the sternum and emerge through the intercostal spaces on both sides of the sternum and attached to the plate by threading through the slots. Before or after the male end is threaded through the female slot with locking mechanism the cardiac needle can be removed from the end and the fastener can be tensioned pulling the sternum fragments closed. Once the chest wall is sufficiently closed the excess fastener end can be trimmed back and removed leaving the fastener flush at the surface of the locking slot. Alternatively, a special cannulated awl could be used to tunnel under the sternum easing the passage of fasteners without the use of cardiac needles.

The cannulated tensioning handle can be used to tension the fasteners to enable closure of the open sternum. This is done by engaging the end of the fasteners with the handle so that the handles can be pulled with human power to provide tension on the fasteners pulling against the strut plate and close the sternum. After tensioning the handles can be released from the fasteners and the handles can be disposed.

The sternum plate covers the sternum body and manubrium and is affixed to the bony anatomy with zip tie-like strap fasteners that pass behind the sternum and lock to or through the plate that is placed on the forward facing aspect of the sternum and manubrium. When secured in place the device assembly supports and holds the surgically cut bones and their attachments in anatomical approximation effectively holding close the chest wall by compressing together along the cut or fractured bone surfaces promoting reduced pain or pain free healing of the sternum and surrounding tissues while at the same time allowing the flexibility for the chest cavity to expand and contract during breathing, coughing and other physiological loading. The fasteners interact with the sternum strut plate by attaching to it through the slots and compressing the device assembly around the bony fragments when tensioned bringing the surgically cut bone ends into direct contact to promote biological healing with bony union.

Figure 13:
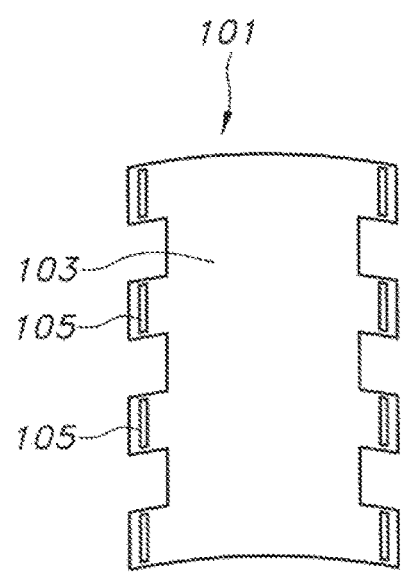
FIG. 13 shows a female portion of an two plate embodiment of the invention.
Figure 14:
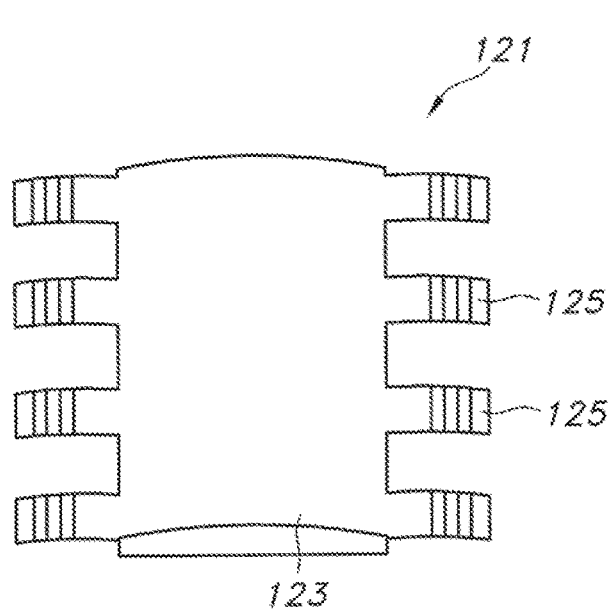
FIG. 14 shows a male portion of an two plate embodiment of the invention.

FIGS. 13 and 14 show a dual plate embodiment of the invention where a female circumfixation plate 101 and a male circumfixation plate 121 may be joined and fastened around a bone or bone fragments to aid in the stabilization and union of the bone. The female plate 101 possesses a plurality of apertures 103, each aperture having a self locking fastener mechanism. The male plate 121 possesses a plurality of fastener straps 125 built into and extending out from the plate body 123. The male plate 121 may be positioned upon one side of the bone, or bone fracture, while the female plate 101 is positioned upon the opposite side. The fattener straps 125 are fed through the apertures 105 and tightened to secure the plates 101, 121 together. The excess straps 125 may then be trimmed flush with the female plate body 103.

Figure 15:
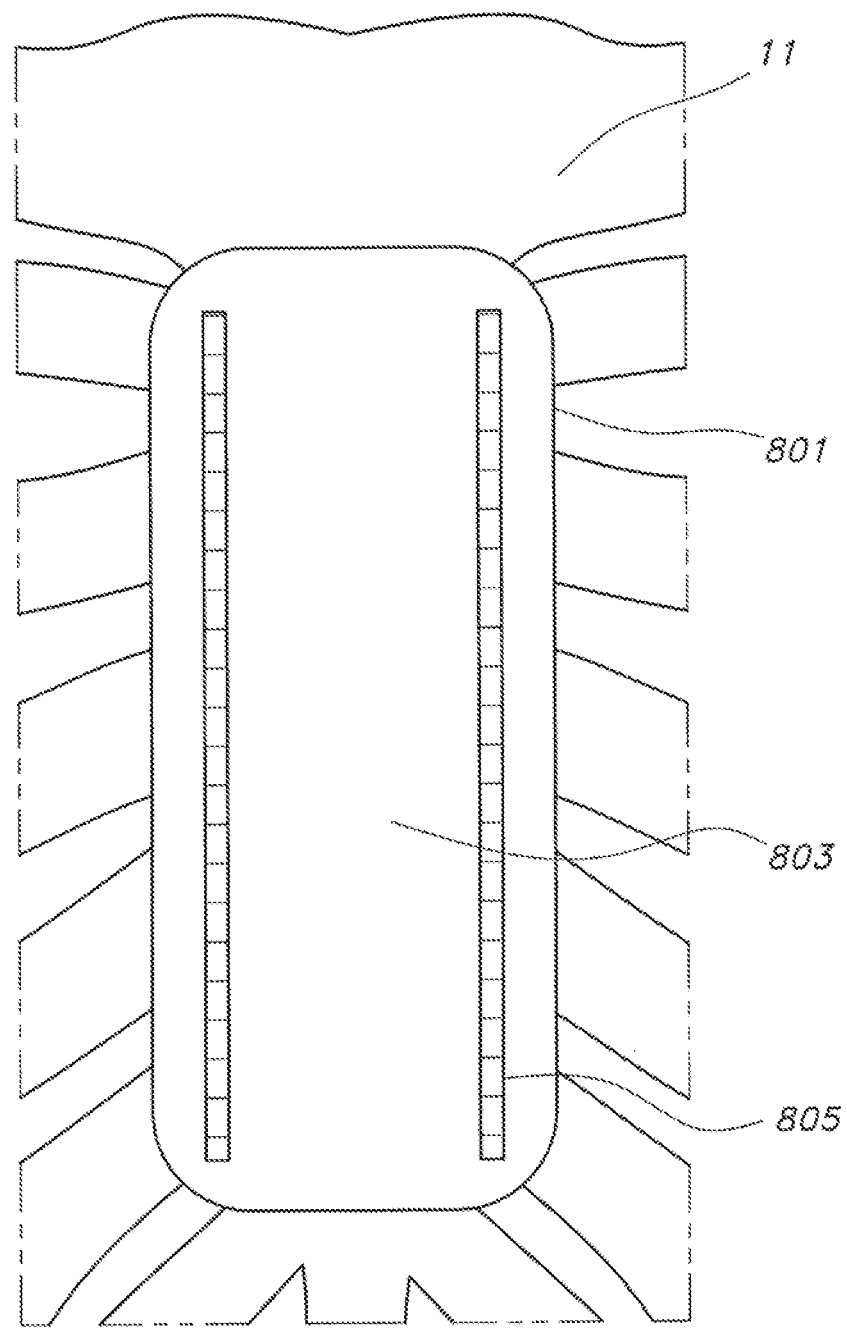
FIG. 15 shows an embodiment of the invention having a plurality of apertures spaced in close proximity along each side of the plate.

FIG. 15 shows the sternum 11 and yet another embodiment 801 having a plurality of closely spaced apertures 805, or slots positioned along the left and right sides of the plate body 807. Due to the variability of patient specific rib spacing such a design may be more practical by providing the operator more options to dock fasteners to the sternum plate.

Figure 16:
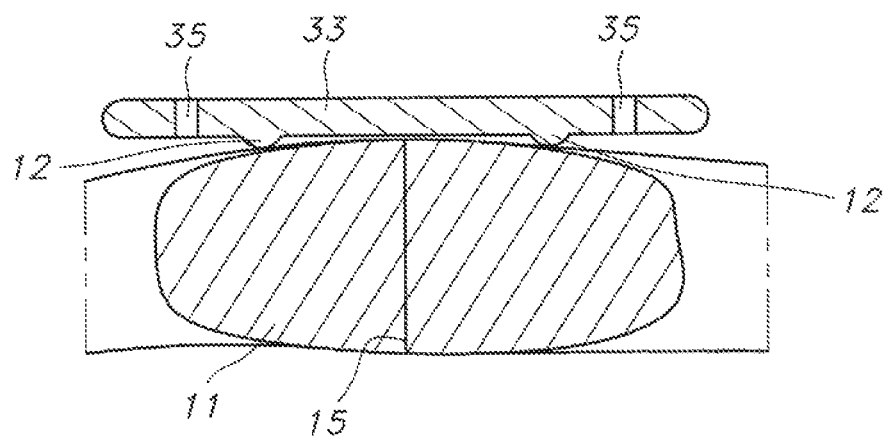
FIG. 16 is a section view taken along line 16-16 of FIG. 2.

FIG. 16 shows a cross section of the sternum and invention taken on line 1616 from FIG. 2. The torsion rails provide for a reduced surface contact area with the bone, allowing increased circulation of bodily fluids to the bone and other tissues. The torsion rails also provide additional stiffness to the plate.

Overall, then, as described herein, the technique referred to as circumfixation could have applications in rib fracture fixation, clavicle fracture fixation, scapula fracture fixation, proximal and distal femur fixation, proximal and distal tibia fixation, fibula fixation, proximal and distal humerus fixation, proximal and distal radius and ulna fixation, wrist bracing and/or reconstruction, ankle bracing and/or reconstruction, spinal bracing and/or reconstruction, pediatric fracture fixation, periprosthetic fracture management and fixation, veterinary fracture fixation and possibly other unidentified applications. The general invention thus comprises, in terms of post sternotomy (and the like) surgical procedures, a plate contoured to lie passively against the forward facing aspect of the human sternum when placed directly on the irregular surface of the target sternum, and zip tie-like fasteners to secure the plate around the target sternum, thus securing the plate to the target sternum. Thus, the herein described invention allows for a reduction postoperative pain for the target patient as well as early postoperative mobilization thereof. Such beneficial activities may thus lead to earlier rehabilitation and discharge, and also accord a reduced potential for infection (as well as a reduced propensity to contract hospital-acquired pathogens). The device is intended to be biocompatible allowing it to remain in the body permanently, too. The device is intended to be inert and radiolucent causing no interference with any testing, diagnostic or imaging technology applied to the patient postoperatively.

It should be understood that various modifications within the scope of this invention can be made by one of ordinary skill in the art without departing from the spirit thereof. It is therefore wished that this invention be defined by the scope of the appended claims as broadly as the prior art will permit, and in view of the specification if need be.

What is claimed is:

1. A plate, comprising:
   two substantially parallel longitudinal sides and two latitudinal ends, wherein said plate is contoured to lie passively against the forward facing aspect of a human sternum when placed directly on a surface of the sternum, and said plate is tapered so that it will conform to the general shape of the sternum and angled upward so as to accommodate a rise of the sternum at the junction of the sternum and manubrium, said plate configured to receive a plurality of tie fasteners thereby attaching said tie fasteners to portions of said longitudinal sides, and the plate further being configured to hold said plate on said surface of the sternum when attached around the bottom surface of said bone and tensioned.

2. The plate of claim 1, wherein said tie fasteners are zip tie-like fasteners having attachable cannulated handles for fastener manipulation and tensioning.

3. The plate of claim 1, wherein said fasteners are cannulated with an interior core to accommodate a guide wire.

4. The plate of claim 1, wherein said plate is capable of carrying and releasing or being coated with and releasing therapeutic agents selected from the group consisting essentially of antibiotics, bone healing agents, pain relievers, cancer treatments, and combinations thereof.

5. The plate of claim 1, wherein at least one of said tie fasteners is a single ended locking fastener.

6. The plate of claim 5, wherein said tie fastener further comprises a head at a non-locking end configured to rest flush upon being threaded through a non-locking slot and meeting a surface of said plate.

7. The plate of claim 1, wherein at least one of said tie fasteners is a double ended locking fastener having first and second ends, wherein both ends of the fastener are configured for locking engagement with the plate through slots containing locking mechanisms such that both ends can be simultaneously tensioned at opposing sides of the plate.

8. The plate of claim 7, wherein said at least one tie fastener is a zip tie-like fastener having an attachable cannulated handle at least one end for fastener manipulation and tensioning.

9. The plate of claim 7, wherein said at least one tie fastener is cannulated with an interior core to accommodate a guide wire.

* * * * *